US012083291B2

(12) United States Patent
Molina et al.

(10) Patent No.: US 12,083,291 B2
(45) Date of Patent: Sep. 10, 2024

(54) ANCHORING DEVICES FOR IMPLANTED TUBES AND RELATED METHODS

(71) Applicant: Regents of the University of Minnesota, Minneapolis, MN (US)

(72) Inventors: Marcos Molina, Orlando, FL (US); Jennifer Kim, Madison, WI (US); Joshua Cadavez, Plano, TX (US); Grace Joseph, Minneapolis, MN (US); Nicholas Gulachek, Minneapolis, MN (US); Arthur G. Erdman, New Brighton, MN (US); Paul Rothweiler, Stillwater, MN (US); Aaron Paul Tucker, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 946 days.

(21) Appl. No.: 17/046,411

(22) PCT Filed: Apr. 9, 2019

(86) PCT No.: PCT/US2019/026585
§ 371 (c)(1),
(2) Date: Oct. 9, 2020

(87) PCT Pub. No.: WO2019/199829
PCT Pub. Date: Oct. 17, 2019

(65) Prior Publication Data
US 2021/0106789 A1 Apr. 15, 2021

Related U.S. Application Data

(60) Provisional application No. 62/655,112, filed on Apr. 9, 2018.

(51) Int. Cl.
*A61M 25/02* (2006.01)
*A61B 5/03* (2006.01)
(Continued)

(52) U.S. Cl.
CPC ............. *A61M 25/02* (2013.01); *A61B 5/031* (2013.01); *A61J 15/0061* (2013.01); *A61M 1/04* (2013.01);
(Continued)

(58) Field of Classification Search
CPC ........ A61M 25/02; A61M 1/04; A61M 39/20; A61M 2025/024; A61M 2025/0266; A61M 2205/0205; A61B 5/031; A61J 15/0061
See application file for complete search history.

(56) References Cited

U.S. PATENT DOCUMENTS 3,046,984 A 7/1962 Eby
3,574,306 A 4/1971 Alden
(Continued)

FOREIGN PATENT DOCUMENTS

WO WO-2019199829 A1 10/2019

OTHER PUBLICATIONS

"International Application Serial No. PCT/US2019/026585, International Preliminary Report on Patentability mailed Oct. 22, 2020", 9 pgs.
(Continued)

*Primary Examiner* — Benjamin J Klein
*Assistant Examiner* — Rachel O'Connell
(74) *Attorney, Agent, or Firm* — Schwegman Lundberg & Woessner, P.A.

(57) ABSTRACT

A device includes a base and a tube clamp. The tube clamp is coupled to an upper surface of the base. The assembled tube clamp and base are positioned around a tube and moved into engagement with a surface of a patient, at which point a lower surface of the base is adhered to the surface of the patient to anchor the tube relative to the surface of the patient.

13 Claims, 5 Drawing Sheets

(51) Int. Cl.
*A61J 15/00* (2006.01)
*A61M 1/04* (2006.01)
*A61M 39/20* (2006.01)

(52) U.S. Cl.
CPC ....... *A61M 39/20* (2013.01); *A61M 2025/024* (2013.01); *A61M 2025/0266* (2013.01); *A61M 2205/0205* (2013.01)

(56) References Cited

U.S. PATENT DOCUMENTS

| | | | |
|---|---|---|---|
| 3,602,227 A | 8/1971 | Andrew | |
| 4,392,857 A | 7/1983 | Beran | |
| 4,645,492 A * | 2/1987 | Weeks | A61M 25/02 604/174 |
| 4,856,504 A * | 8/1989 | Yamamoto | A61F 13/49009 606/76 |
| 7,232,426 B2 * | 6/2007 | Itrich | A61J 15/0057 604/175 |
| 9,517,327 B2 * | 12/2016 | Khalaj | A61M 25/02 |
| 9,867,969 B2 | 1/2018 | Ward | |
| 10,773,057 B1 * | 9/2020 | LeLievre | A61M 27/00 |
| 2008/0319397 A1 * | 12/2008 | Macaluso | A61J 15/0061 604/174 |
| 2016/0044753 A1 | 2/2016 | Lee | |
| 2023/0218864 A1 * | 7/2023 | Walter-Engelsma | A61M 27/00 604/178 |

OTHER PUBLICATIONS

"Zonnix Chest Tube Fastener", © 2017 [online]. [archived on Sep. 4, 2017]. Retrieved from the Internet: <URL: https://web.archive.org/web/20170904060356/https://adventmedtech.com/zonnix.asp>, (2017), 2 pgs.

Ball, MD, Chad G., et al., "Chest tube complications: How well are we training our residents?", *J Can Surg*, 50(6), (Dec. 2007), 450-458.

Dev, Shelly P., et al., "Chest-Tube Insertion", *N Engl J Med*, 357: e15, (2007), 4 pgs.

"International Application Serial No. PCT/US2019/026585, International Search Report mailed Jul. 3, 2019", 2 pgs.

"International Application Serial No. PCT/US2019/026585, Written Opinion mailed Jul. 3, 2019", 7 pgs.

* cited by examiner

ANCHORING DEVICES FOR IMPLANTED TUBES AND RELATED METHODS

RELATED APPLICATIONS

This application is a U.S. National Stage Application under 35 U.S.C. 371 from International Application Serial No. PCT/US2019/026585, filed on Apr. 9, 2019, and published as WO 2019/199829 A1 and published on Oct. 17. 2019, which claims the benefit of priority to U.S. Provisional Application Ser. No. 62/655,112, filed Apr. 9, 2018, the content of which are hereby incorporated by reference in their entirety.

FIELD

The present disclosure relates to anchoring devices for implanted tubes and related methods.

BACKGROUND

Some medical procedures involve anchoring an implanted tube to the skin of a patient. For example, Tube Thoracostomy is a surgical procedure for removing excess air or fluid from the pleural space of the chest by inserting a tube into the patient through an incision. Some conventional methods include anchoring the tube to the skin of the chest with sutures followed by covering the area with gauze. Some conventional methods can result in relatively long procedure time, tube dislodgement, skin necrosis, infection, improper stabilization of the tube, required daily wound care, enhanced scarring, etc.

BRIEF DESCRIPTION OF THE DRAWINGS

The drawings described herein are for illustrative purposes only of selected embodiments and not all possible implementations, and they are not intended to limit the scope of the present disclosure.

Corresponding reference numerals indicate corresponding parts throughout the several views of the drawings.

DETAILED DESCRIPTION

A tube anchoring device can include a base and a tube clamp. The base can include an adhesive for attaching to the skin of the patient and a hole for receiving a tube (for example, an implanted tube). The tube clamp is attachable to the base and defines a bore configured to receive the tube and a tube exit configured to direct the tube in a selected orientation relative to the skin of the patient. In some examples, at least a portion of the bore has a guide feature disposed therein to provide a smooth pathway for bending the tube from the bore to the tube exit. In some examples, the tube clamp can then be sealed to secure the tube in the selected position and anchor the tube to the skin of the patient. In some examples the tube clamp can further be sealed following removal of the tube, such that the tube exit is sealed. In some examples a tube control cap can engage the tube clamp to seal the incision site and clamp the tube in the selected orientation. In at least one example, the tube control cap can cause the tube to bend toward and engage the tube exit. In some examples, a seal cap can engage the tube clamp to seal the incision site following tube removal. The described tube anchoring device and related methods are more reliable, easier to implement, and more secure than traditional sutures. Additionally, the suture anchoring device and methods can expedite patient care and reduce the occurrence of adverse events caused by tube dislodgement.

The suture anchoring device and associated methods can be useful in various healthcare applications such as, for example and without limitation, a chest tube, a gastrostomy tube, central lines, venous lines, arterial lines, cholecystectomy tubes, Blake tubes, peripheral intravenous lines, intracranial pressure monitoring tubes, and any other drainage or infusion tubing. For clarity, this document explains the present disclosure with reference to a Tube Thoracostomy application, but the applications of the present disclosure are not limited thereto.

Figure 1:
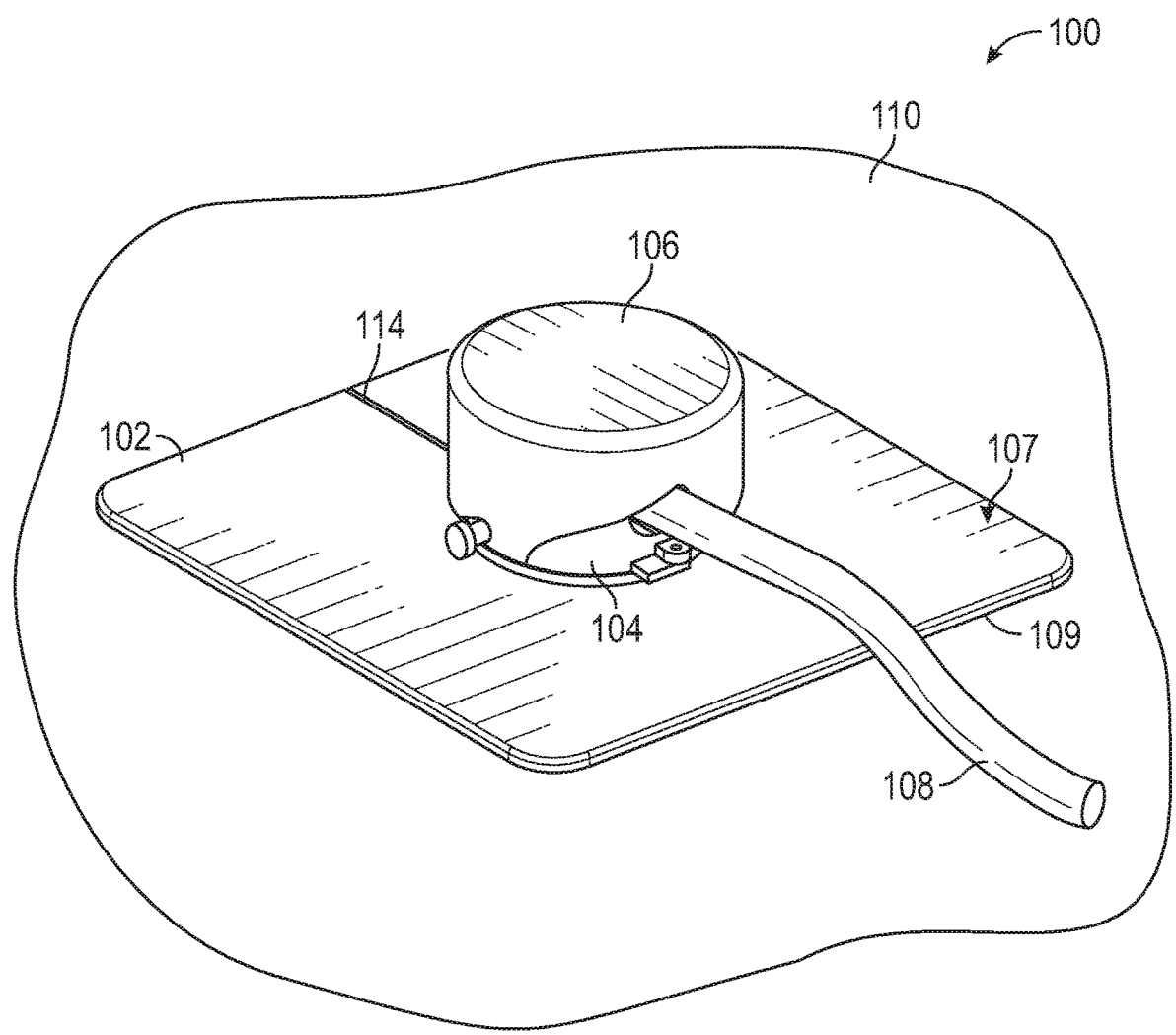
FIG. 1 is a perspective view of a tube anchoring device, in accordance with at least one example.

FIG. 1 illustrates an assembled view of a tube anchoring device 100. The illustrated tube anchoring device 100 includes a base 102, a tube clamp 104, and a tube control cap 106. The tube clamp 104 can be coupled to an upper surface 107 of the base 102. In at least one example, the upper surface 107 of the base 102 includes an adhesive quality configured to adhere to the tube clamp 104. Once assembled, the clamp 104 and base 102 can be positioned around a tube 108 (for example, a tube implanted in a patient as part of Tube Thoracostomy) and can be moved into engagement with a surface 110 of a patient (for example, the skin of a patient's chest), at which point a lower surface 109 of the base 102 can be coupled to the surface 110 of the patient. In the illustrated example, the base 102 includes a slit 114 and the tube clamp 104 is hinged, such that the base 102 and the tube clamp 104 can receive the tube 108. In other examples, the tube 108 may be threaded through the base 102 and the tube clamp 104. In some examples, the base 102 and the tube clamp 104 may be coupled together after one or both has received the tube 108.

Once the base 102 and tube clamp 104 have engaged the tube 108, the tube control cap 106 can engage the tube clamp 104 to secure the tube 108. The tube anchoring device 100 can remain secured to the patient's body without requiring as much maintenance as conventional methods (e.g., the suture-gauze technique). In some examples, the tube anchoring device 100 can be a single use device, such that it is not intended to be reused but instead disposed of once it is removed from the patient.

Figure 2:
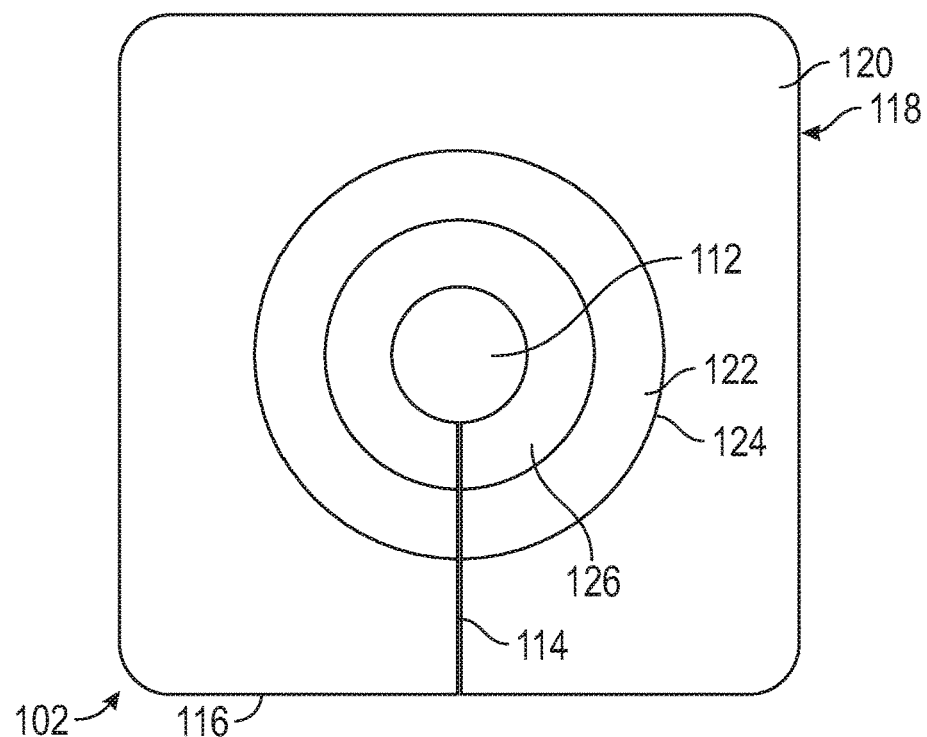
FIG. 2 is a top view of the base of the tube anchoring device of FIG. 1, in accordance with at least one example.

FIG. 2 is a top view of the base 102 of the tube anchoring device 100. In the illustrated example, the base 102 has a hole 112 disposed in a central portion thereof and the slit 114 extends from an edge portion 116 of the base 102 to the hole 112. The slit 114 allows the base 102 to be manipulated so as to separate the slit 114 to receive the tube 108. In other examples, the slit 114 may comprise a larger slot, opening, or cutaway, such that the base portion 102 can receive or otherwise be positioned around the tube 108.

The base can include a bottom layer 118 associated with the lower surface 109 and a top layer 120 associated with the upper surface 107. Each of the top layer 120 and the bottom layer 118 may include an adhesive or have an adhesive quality. In one example, the bottom layer 118 can include a medical grade skin adhesive to secure the base 102 to the surface 110 of the patient. In another example, the top layer 120 can include any suitable adhesive compatible with the tube clamp 104. In some examples, the tube clamp 104 can couple to the base 102 using any of a variety of couplings other than adhesive. In at least one example, the tube clamp 104 and the base 102 are formed as a unitary piece. In at least one example, the base 102 has a shape corresponding to the shape of the bottom surface of the tube clamp 104.

The base 102 can also include an absorptive member 122 that can be disposed surrounding or otherwise adjacent to the hole 112 in contact with an inner edge 124 of the base 102. An outer edge of the absorptive member 122 can be secured between the bottom layer 118 and the top layer 120 along the inner edge 124 of the base 102 such that the top layer 120 and the bottom layer 118 provide structural integrity to the absorptive member 122. In some examples, the absorptive member 122 can be coupled to the bottom layer 118 and the top layer 120 by adhesion, gluing, fusing, or the like. The absorptive member 122 can be absorbent and can help absorb body fluids or any other source of moisture. In at least one example, the absorptive member 122 can comprise a hydrocolloid or any other suitable absorptive material. The absorptive member 122 can also include or be provided in the form of an adhesive tape and can remain adherent in both wet and dry conditions. In some examples, the absorptive member 122 is annular. In at least one example, the absorptive member 122 is segmented. In at least one example, the base is about five inches by five inches (12.7 cm×12.7 cm).

The base 102 can also include an anti-bacterial member 126 that can be disposed interior to and in contact with the absorptive member 122, such that the anti-bacterial member 126 is positioned between the hole 112 and the absorptive member 122. The anti-bacterial member 126 can include chlorhexidine gluconate or any other suitable antimicrobial agent. The anti-bacterial member 126 can be joined to the absorptive member 122 by sewing, suturing, gluing, fusing, or the like. In at least one example the anti-bacterial member 126 is annular. In some examples, the absorptive member 122 and the anti-bacterial member 126 can comprise a single member that provides both absorptive and anti-bacterial properties. In at least one example, the single member can include a silver-hydrocolloid mixture or the like.

Figure 3:
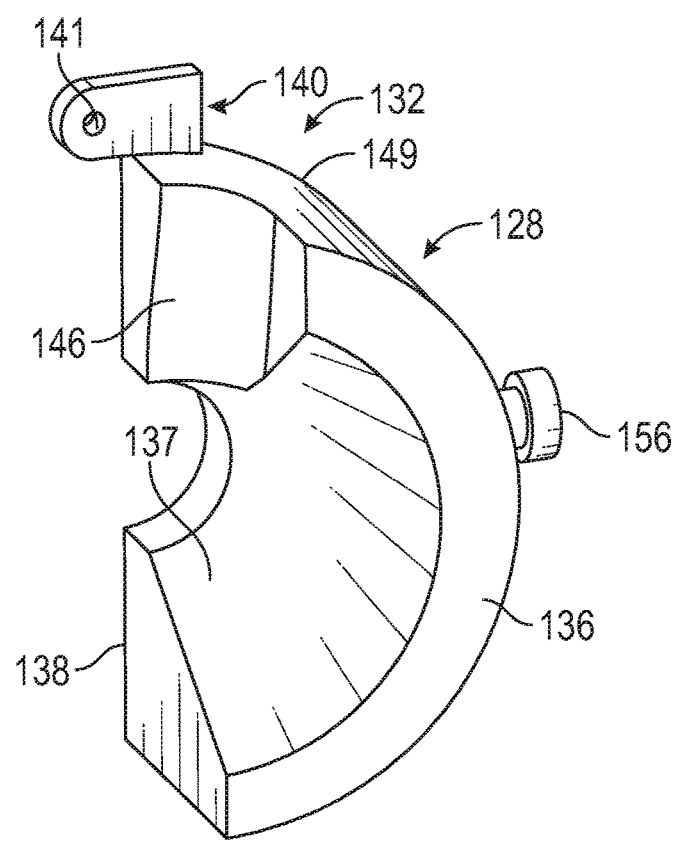
FIG. 3 is a perspective view of a first portion of a tube clamp, in accordance with at least one example.
Figure 4:
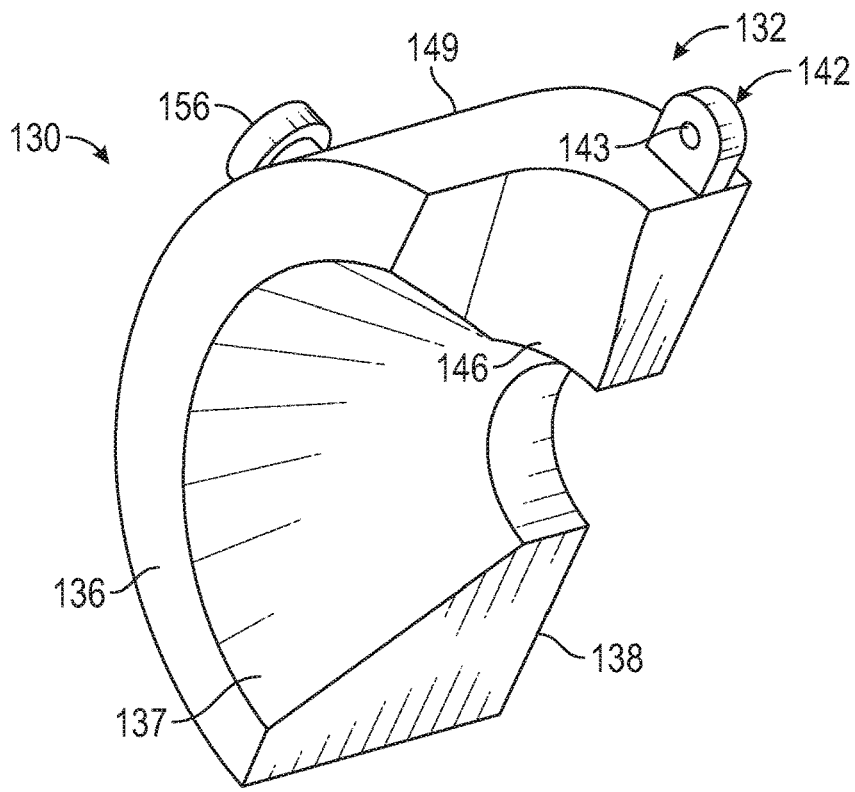
FIG. 4 is a perspective view of a second portion of a tube clamp, in accordance with at least one example.

FIG. 3 is a perspective view of a first portion 128 of the tube clamp 104, and FIG. 4 is a perspective view of a second portion 130 of the tube clamp 104. In the illustrated examples, the first and second portions 128, 130 of the tube clamp 104 include a top surface 136, a bottom surface 138 and a hinge region 132. The first portion 128 is configured to be hinged to the second portion 130 at the hinge region 132 of the tube clamp 104. The first portion 128 and the second portion 130 can cooperate to define a bore 134 extending from the top surface 136 to the bottom surface 138 of the tube clamp 104 to engage the tube 108. The first portion 128 can include a first bracket 140 having a hole 131 mate-able with a hole 143 of a second bracket 142 extending from the second portion 130 at the hinge region 132. The first bracket 140 and the second bracket 142 can be joined by a pin 144 (see FIG. 6) aligned with a longitudinal axis of the mating holes 141, 143 of the brackets 140, 142. In at least one example, when the pin 144 extends through the holes 141, 143, a longitudinal axis of the pin 144 is parallel to a longitudinal axis of the bore 134. In the illustrated example, the first and second portions 128, 130 of the tube clamp 104 are hinged to allow the tube clamp 104 to be opened to receive the tube 108 and then closed around the tube 108. In other examples, rather that two portions hinged, the tube clamp 104 can include two or more portions that can be coupled or otherwise assembled around the tube 108 using any of a variety of couplings. In at least one example, the tube clamp 104 can be threaded over the tube 108. Such an example of the tube clamp 104 would not require multiple portions or opening of the tube clamp 104 to receive the tube 108.

In some examples, a tube exit 146 extends from the bore 134 to a sidewall 149 of the tube clamp 104. In at least one example, the tube exit 146 can be positioned at the hinge region 132 of the tube clamp 104. In at least one example, aligning the tube exit 146 and the hinge region 132 allows for easy one-handed placement of the tube clamp 104. In some examples, at least a portion of the bore 134 can have a guide feature 137 disposed therein to provide a smooth pathway for bending the tube from being substantially perpendicular to the surface 110 of the patient at the bore 134 proximate the bottom surface 138 to extending through at least one of the tube exit 146 and the bore 134 proximate the top surface 136. This can reduce the side forces applied to the tube at the bottom surface 138, thereby reducing or eliminating patient discomfort. In at least one example, the tube exit 146 can extend through a top surface of the tube clamp 104 (for example, the top surface 136 of the tube clamp 104 can extend over the entire tube clamp 104, and the tube exit 146 can be formed through this top surface). In some examples, the tube clamp 104 can be formed from PVC, PMMC, silicone rubber, or the like. In at least one example, the tube clamp 104 is formed of metal. In some examples the tube clamp 104 comprises a thermoplastic.

For ease of illustration and explanation, the tube clamp 104 has been described with reference to first and second portions 128, 130 that are hinged, however a variety of configurations of a tube clamp 104 are possible, so long as they allow for receipt of the tube 108 and can subsequently allow for a seal (e.g., a seal sufficient to protect the wound from germs). In some examples, the tube clamp 104 additionally allows for redirection of the tube 108, for example through the tube exit 146. In some examples, the first and second portions 128, 130 are configured to receive the tube 108 in an uncoupled state, and to capture the tube in the coupled state 128, 130. That is, in the uncoupled state, the first and second portions 128, 130 provide an opening or otherwise allow the tube 108 to be received in the bore 134, and in the coupled state, the opening is no longer provided, such that the tube 108 is captured in at least a portion of the bore 134. In some examples, the first and second portions 128, 130 may be at least partially coupled together in the uncoupled state such that they are connected but still define an opening or otherwise allow access to the bore 134 by the tube 108, and they are further coupled together to close this access or opening.

In one such variation, the first portion 128 can comprise an inner ring that has a slot such that the ring comprises a semicircle and allows for receipt of the tube 108. The second portion 130 can comprise a sleeve that can partially or fully extend around the perimeter of the first portion 128. In at least one example, the second portion 130 conforms to the outer surface of the first portion 128 along its periphery including filling in the slot for receiving the tube 108, such that it allows for a seal to be formed. The seal helps protect the incision site covered by the device from germs and other foreign bodies. In some examples the seal is a substantially airtight seal. In some examples, the seal is an intentional barrier sufficient to keep out unwanted foreign bodies. In some examples the first and second portions 128, 130 may include one or more mating features or connectors to secure the second portion 130 to the first portion 128. In at least one example, the second portion 130 is removably coupled to the first portion 128. In at least one example, the first portion 128 and the second portion 130 can be connected via a snap-fit. In some examples, the first portion 128 includes a tube exit 146, in some examples the second portion 130 includes the tube exit 146, and in other examples, the tube exit 146 is included in both the first and second portions 128, 130. The tube clamp 104 can include one or more coupling features similar to those described above with reference to FIGS. 3 and 4 for coupling to one or more caps (e.g., the tube control cap 106, or a seal cap 160 (see FIG. 7).

In at least one example, the cap feature can be integrated into the tube clamp 104, such that the tube clamp 104 can create a seal over the wound and control the orientation of the tube 108 without the use of an additional cap 106, 160. In such an example, the tube clamp 104 can include an opening to receive the tube and a tube exit 146, each of which can be sealed by a feature of the tube clamp 104. For example, a hinged element, a sliding element, a snap-fit element, a plug, a combination of these, or the like could be used to fill or cover an opening to facilitate a seal of the wound cover (e.g., a substantially airtight seal or other barrier sufficient to prevent foreign bodies such as germs from interfering with the wound site). In some examples, the tube clamp 104 could use a first closing feature to close a portion of an opening to control (e.g., clamp, secure, or control the orientation of) the tube 108, and a second closing feature to close the remainder of the opening once the tube 108 has been removed such that the tube anchoring device 100 can provide a seal over the wound. For example, the first closing feature could be a hinged or sliding element (or a first plug) that limits the orientation of the tube 108 by creating a smaller opening, and once the tube 108 is removed, the smaller opening can be sealed with the second closing feature, for example a second plug, hinged element, or sliding element. In some examples, a living hinge can be used.

Figure 5:
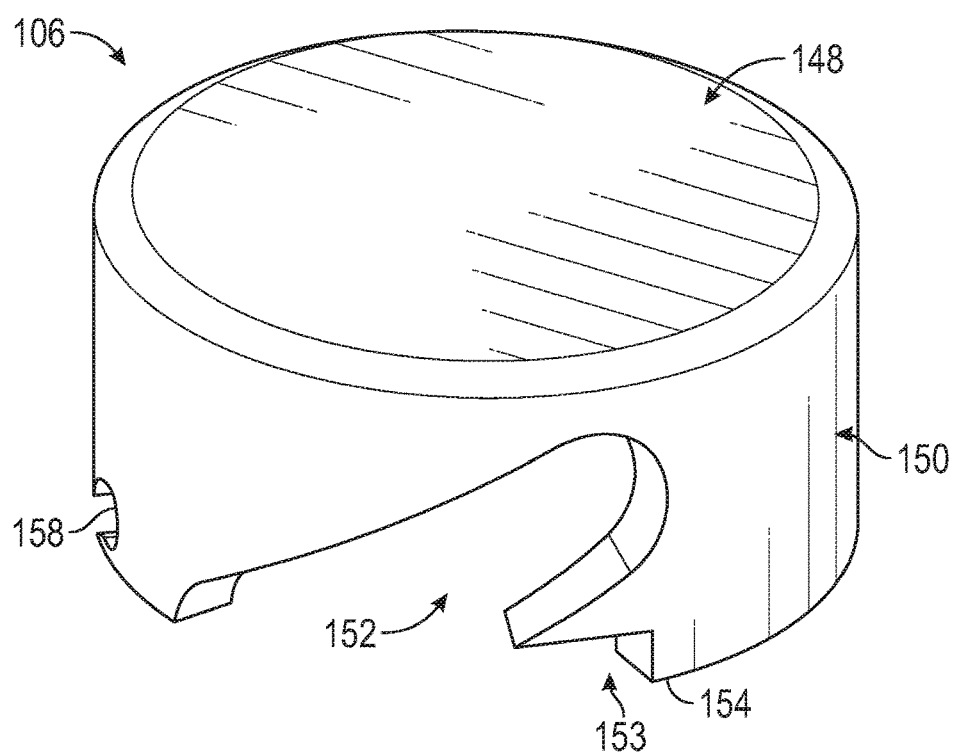
FIG. 5 is a perspective view of a tube control cap, in accordance with at least one example.

FIG. 5 is a perspective view of the tube control cap 106, in accordance with at least one example. As illustrated, the tube control cap 106 includes a top surface 148 and a sidewall 150 extending therefrom. A tube slot 152 can be disposed in the sidewall 150 and can extend from the free end 154 of the sidewall 150 toward the top surface 148. In at least one example, the tube slot 152 extends at an acute angle relative to the top surface 148, for example, to accommodate the tube 108 as the tube control cap 106 is lowered and rotated over the tube clamp 104. The tube control cap 106 can be rotatably engageable with the tube clamp 104 to retain the tube 108 engaged by the tube clamp 104. In some examples, the tube control cap 106 and the tube clamp 104 work together to retain the tube 108 in a specific orientation or a specific range or orientations, for example an orientation that is not perpendicular to the surface 110 of the patient. In at least one example, the tube control cap 106 and the tube clamp 104 work together to immobilize the tube 108. In at least one example, the tube control cap 106 and the tube clamp 104 work together to retain the tube 108 in an orientation that is nearly parallel to the surface 110 of the patient. In some examples, the tube control cap 106 and the tube clamp 104 work together to control the tube 108, for example, to clamp, secure, or otherwise limit the movement of the tube 108.

In some examples, the tube clamp 104 and the tube control cap 106 have complementary features to retain the tube clamp 104 and the tube control cap 106 in fixed alignment with one another. In at least one example, these complementary features allow assembly or disassembly by manual manipulation without requiring tools or secondary fastener devices. Such complementary features can include, for example and without limitation, those of cam-lock fasteners, quarter-turn fasteners, fractional-turn fasteners, bayonet mounts, mating threads, or the like. In some examples, the tube clamp 104 can include at least one peg 156 extending from an exterior surface of the tube clamp 104. In the illustrated examples, the tube clamp 104 includes two pegs 156 extending perpendicular to the axis of the bore 134. In the illustrated examples, each of the first and second portions 128, 130 includes a peg 156, such that each portion 128, 130 is directly secured to the tube control cap 106.

The tube control cap 106 can have at least one contoured slot 158 disposed therein for receiving a corresponding one of the at least one peg 156 to secure the tube control cap 106 to the tube clamp 104 upon engagement and rotation relative to the peg 156. In the illustrated examples, the tube control cap 106 includes two contoured slots 158 to correspond to the two pegs 156 of the tube clamp 104. In some examples, one of the tube clamp 104 and the tube cap 106 can be a male side of a bayonet mount and the remaining one can be a female side of a bayonet mount. In some examples, the tube control cap 106 includes a hinge slot 153 configured to accommodate the hinge region 132 of the tube clamp 104.

Figure 6:
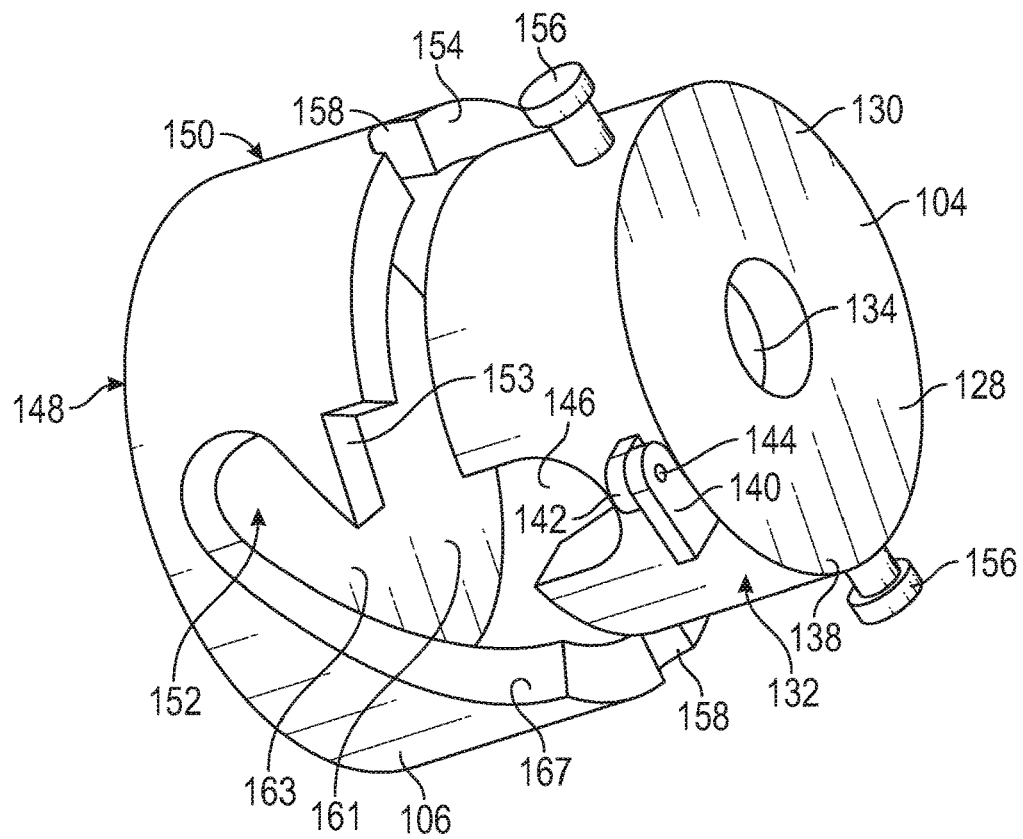
FIG. 6 is an exploded perspective view of the tube control cap of FIG. 5 and the tube clamp of FIGS. 3 and 4, in accordance with at least one example.

FIG. 6 is an exploded perspective view of the tube control cap 106 of FIG. 5 and the tube clamp 104 of FIGS. 3 and 4 aligned for engagement. In the illustrated example, the pegs 156 of the tube clamp 104 are aligned with the contoured slots 158 of the tube control cap 106, the tube exit 146 of the tube clamp 104 is aligned with the tube slot 152 of the tube control cap 106, and the hinge region 132 of the tube clamp 104 is aligned with the hinge slot 153 of the tube control cap 106 (note that in this example, there is overlap in the tube slot 152 and the hinge slot 153). In the illustrated example, the contoured slots 158 can be placed over the pegs 156, and the tube control cap 106 rotated such that the pegs 156 follow the contoured slots 158, and the hinge region 132 moves within the hinge slot 153. In at least one example, a guide surface 167 of the tube control cap 106 helps define the tube slot 152 and can guide the tube 108 as the tube control cap 106 is coupled to the tube clamp 104. In at least one example, the tube control cap 106 can include an inner surface 163 opposite the top surface 148 that can include an anti-bacterial material 161 such as an antimicrobial sponge, a hydrocolloidal gel, or the like. In at least one example, the antimicrobial material 161 is configured to absorb body fluids and remove bad bacteria and germs. In some examples, the tube control cap 106 can aid in infection prevention and tube stabilization.

While the illustrated examples show the tube control cap 106 rotatably engaging the tube clamp 104, in some examples, the tube control cap 106 can be configured to slide over the tube clamp 104 to control the tube 108 (e.g., clamp, secure, or otherwise limit the orientation of the tube 108). The tube control cap 106 and the tube clamp 104 can include corresponding mating features (e.g., tongue and groove) to allow the tube control cap 106 to engage and couple to the tube clamp 104 by sliding over the tube clamp 104. In such an example, the tube control cap 106 can include a tube slot 152 to control the tube 108 as the tube control cap 106 slides over the tube clamp 104.

Figure 7:
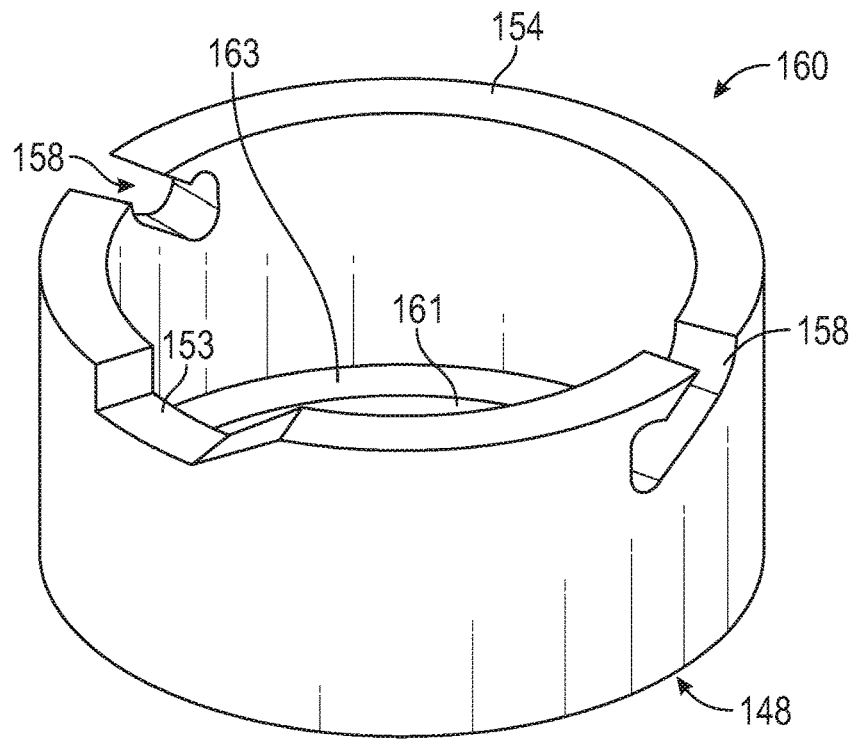
FIG. 7 is a perspective view of a seal cap, in accordance with at least one example.

FIG. 7 is a perspective view of a seal cap 160 which can be provided to seal the tube clamp 104 subsequent to removal of the tube 108. In some examples, the seal cap 160 can be substantially similar to the tube control cap 106 except that the seal cap 160 does not include the tube slot 152, since it is not accommodating the tube 108 and would need to seal the tube exit 146 of the tube claim 104. In some examples, the seal cap 160 includes the contoured slots 158 (or other coupling mechanism corresponding to that of the tube clamp 104) and the hinge slot 153 (or other features to accommodate the tube clamp 104). In at least one example, the seal cap 160 can include an inner surface 163 opposite the top surface 148 that can include an anti-bacterial material 161 such as an antimicrobial sponge, hydrocolloidal gel, or the like. In at least one example, the antimicrobial material 161 is configured to absorb body fluids and remove bad bacteria and germs. In some examples, the seal cap 160 can aid in infection prevention. In at least one example, the seal cap 160 provides a seal of the incision site (or wound) and helps to prevent infection. In some examples, the seal cap 160 helps to prevent re-expansion of the pneumothorax. In at least one example, the seal cap 160 facilitates proper healing of the incision site.

In at least one example, instead of including a separate seal cap 160, the tube anchoring device 100 can use the tube control cap 106 for sealing once the tube 108 has been removed. For example, the tube control cap 106 can be rotated so that the tube slot 152 does not align with the tube exit 146, thereby sealing the tube clamp 104. That is, with reference to the illustrated examples, the tube control cap 106 can be aligned with the tube clamp 104 in an orientation that is rotated 180 degrees relative to that which is shown, such that the tube slot 152 is positioned on the opposite side of the tube clamp 104 from the tube exit 146, but such that the pegs 156 still align with the contoured slots 158. In some examples, the tube control cap 106 can be rotated relative to the tube clamp 104 (when the tube clamp 104 is not engaging the tube 108) to seal the incision site and help prevent infection. In some examples, a plug can be provided that can be secured in the tube exit 146 of the tube clamp 104. In some examples, the plug can seal the incision site and help prevent infection. In some examples, the seal cap 160 can be integrated into the tube clamp 104 or the tube control cap 106. For example, a closing element (e.g., a plug, a hinged element, a sliding element, a combination of these or the like) can be configured to close the opening (e.g. the tube slot 152/tube exit 146).

In some examples, one or more elements of the tube anchoring device 100 can comprise a thermoplastic. In some examples, one or more elements of the tube anchoring device 100 can be formed using injection molding. In some examples, the base 102 comprises a split hydrocolloid. In at least one example, the tube clamp 104 and the caps 106, 160 each comprise a thermoplastic. While the illustrated examples show the base 102 with a square shape, any of a variety of shapes could be used. Further, while the illustrated examples of the tube clamp 104 and caps 106, 160 include a substantially circular circumference, any of a variety of geometries could be used to sufficiently anchor the tube and provide a seal following tube removal.

In some examples, the tube clamp 104 can be configured to create a seal around the tube 108 without a cap 106. In some examples, the tube clamp 104 can be configured to create a seal around the tube 108 with a cap 106. In some examples the tube clamp 104 can be configured to create a seal once the tube is removed without a cap 160. In some examples, the tube clamp 105 can be configured to create a seal once the tube is removed with a cap 160. In some examples, a gasket or the like can be used with the tube clamp 104 or cap 106, 160 to facilitate forming the seal.

Figure 8:
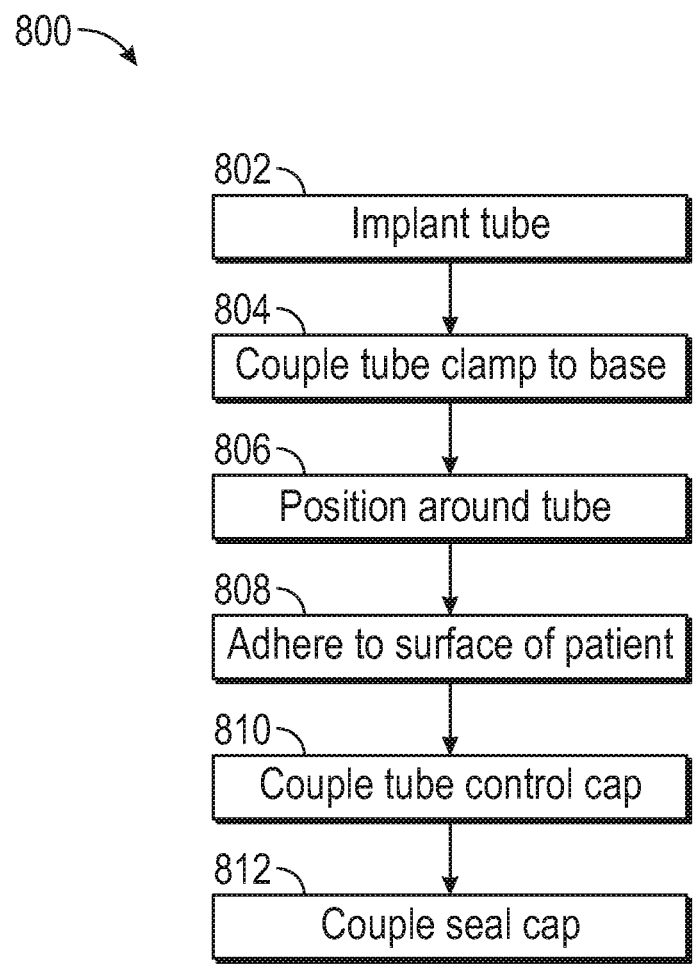
FIG. 8 is a is a flow chart of a method, in accordance with at least one example.

FIG. 8 illustrates an example method 800 of the present disclosure. At block 802, a tube 108 can be placed through an incision in a surface 110 of a patient. For example, the tube 108 can be placed in the chest as part of a Tube Thoracostomy procedure. In some examples, the tube 108 can be a chest tube, a gastrostomy tube, central lines, venous lines, arterial lines, cholecystectomy tubes, Blake tubes, peripheral intravenous lines, intracranial pressure monitoring tubes, and any other drainage or infusion tubing.

At block 804, the tube clamp 104 can be adhered to the top surface 107 of the base 102. In at least one example, the tube clamp 104 and base 102 are assembled such that the first and second portions 128, 130 of the tube clamp 104 are disposed on opposite sides of the slit 114 disposed in the base 102.

At block 806, the assembled base 102 and tube clamp 104 can then be positioned around the tube 108. In at least one example, the base 102 can separate at the slit 114, and the tube clamp 104 can open due to its hinge region 132 to receive the tube 108. In other examples, the assembled base 102 and tube clamp 104 can be threaded over the tube 108. In some examples, the base 102 may comprise a plurality of modular parts each adhered to one of a plurality of portions of the tube clamp 104, and the portions of the tube clamp 104 can be assembled around the tube 108.

At block 808, the bottom surface 109 of the base 102 can be adhered to the surface 110 of the patient. In another example, the base 102 can be attached to the surface 110 of the patient before the tube clamp 104 is attached to the base 102. In at least one example, the tube 108 can be placed through the tube exit 146 of the tube clamp 104.

At block 810, the tube control cap 106 can be rotated relative to the tube clamp 104 such that the tube 108 is guided into the space defined by the tube exit 146 and the tube slot 152, and such that the pegs 156 engage the contoured slots 158 to couple the tube control cap 106 to the tube clamp 104. In at least one example, the tube 108 is immobilized when the tube control cap 106 is coupled to the tube clamp 104.

At block 812, the tube control cap 104 is removed and the tube 108 is pulled out. At block 120, the tube clamp 104 is sealed, for example using a seal cap 160, by reusing the tube control cap 104 at a different orientation, or by using a plug.

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Use of the word "seal" can mean a seal or barrier sufficient to prevent foreign objects (e.g., germs) from entering the incision site or wound surrounded by the device. For example, a "seal" could limit airflow sufficient to avoid interference by foreign bodies that could lead to infection. In some examples "seal" can mean a substantially airtight seal.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

What is claimed is:

1. A device, comprising:
   a base defining a hole in a central portion thereof and a slit extending from an edge portion of the base to the hole, wherein a bottom surface of the base includes an adhesive;
   a tube clamp coupled to a top surface of the base, the tube clamp including a first portion and a second portion configured to be coupled together, wherein the tube clamp defines a bore extending from a bottom surface to the top surface, wherein the tube clamp defines a tube exit extending from the bore through a sidewall of the tube clamp; and
   wherein the base and tube clamp are configured to be positioned around a tube implanted in a patient and to anchor the tube to a surface of the patient; and further comprising
   a tube control cap configured to engage the tube clamp to clamp the tube.

2. The device of claim 1, wherein:
   the tube clamp comprises a peg extending from an exterior surface of the tube clamp; and
   wherein the tube control cap has a contoured slot, for receiving the peg to secure the tube control cap to the tube clamp.

3. The device of claim 1, wherein:
   the tube clamp comprises a male side of a bayonet mount; and
   the tube control cap comprises a female side of a bayonet mount.

4. The device of claim 1, wherein the tube control cap further includes an antimicrobial material at an inner surface.

5. The device of claim 1, further comprising:
   a seal cap configured to engage the tube clamp to create a seal.

6. A device, comprising:
   a base defining a hole in a central portion thereof and a slit extending from an edge portion of the base to the hole, wherein a bottom surface of the base includes an adhesive;
   a tube clamp coupled to a top surface of the base, the tube clamp including a first portion and a second portion configured to be coupled together, wherein the tube clamp defines a bore extending from a bottom surface to the top surface, wherein the tube clamp defines a tube exit extending from the bore through a sidewall of the tube clamp; and
   wherein the base and tube clamp are configured to be positioned around a tube implanted in a patient and to anchor the tube to a surface of the patient, and
   wherein the second portion is configured to couple to the first portion via a snap-fit.

7. A device, comprising:
   a base including an adhesive at a bottom surface such that the base is configured to adhere to a surface of a patient, the base defining a hole configured to receive a tube implanted in the patient;
   a tube clamp configured to couple to a top surface of the base, the tube clamp defining a bore at a bottom surface of the tube clamp, the bore configured to receive the tube, the tube clamp defining a tube exit extending from the bore through a sidewall of the tube clamp; and
   a tube control cap configured to couple to the tube clamp to control the orientation of the tube, such that the tube extends through the hole of the base, through the bore at the bottom surface of the tube clamp, and out the tube exit defined by the sidewall of the tube clamp.

8. The device of claim 7, further comprising:
   a seal cap configured to couple to the tube clamp to create a seal.

9. The device of claim 7, wherein the tube clamp comprises first and second portions hinged together, such the tube clamp is opened to receive the tube.

10. The device of claim 7, wherein the tube clamp further comprises a guide feature configured to guide the tube as it bends from the bore to the tube exit.

11. The device of claim 7, wherein the tube control cap further comprises a guide surface configured to guide the tube into a selected orientation relative to the surface of the patient.

12. The device of claim 7, wherein:
   the tube clamp includes a first portion of a bayonet mount; and
   the tube control cap includes a second portion of the bayonet mount, wherein the first and second portions of the bayonet mount are configured to mate.

13. A method, comprising:
coupling a tube clamp to a top surface of a base, the base defining a hole and the tube clamp defining a bore extending from a bottom surface to a top surface of the tube clamp;
positioning the tube clamp and base around a tube implanted in a patient such that the tube extends through the hole of the base and the bore of the tube clamp;
adhering a bottom surface of the base to a surface of the patient;
moving the tube to a bore exit defined by a sidewall of the tube clamp; and
clamping, with the tube clamp, the tube in a selected orientation relative to the surface of the patient; further comprising:
positioning a tube control cap over the tube clamp to facilitate the clamping of the tube;
removing the tube control cap from the tube clamp;
removing the tube from the tube clamp and the base; and
positioning a seal cap over the tube clamp to create a seal.

* * * * *

UNITED STATES PATENT AND TRADEMARK OFFICE
CERTIFICATE OF CORRECTION

| | |
|---|---|
| PATENT NO. | : 12,083,291 B2 |
| APPLICATION NO. | : 17/046411 |
| DATED | : September 10, 2024 |
| INVENTOR(S) | : Molina et al. |

Page 1 of 1

It is certified that error appears in the above-identified patent and that said Letters Patent is hereby corrected as shown below:

In the Specification

In Column 3, Line 61, delete "131" and insert --141-- therefor

In Column 7, Line 10, delete "claim" and insert --clamp-- therefor

In Column 8, Line 3, delete "105" and insert --104-- therefor

In Column 8, Line 47, delete "104" and insert --106-- therefor

In Column 8, Line 50, delete "104" and insert --106-- therefor

In the Claims

In Column 9, Line 65, in Claim 1, after "comprising", insert --:--

Signed and Sealed this
Ninth Day of September, 2025

Coke Morgan Stewart
*Acting Director of the United States Patent and Trademark Office*